United States Patent [19]

Heinemann

[11] 4,447,150
[45] May 8, 1984

[54] APPARATUS AND METHOD FOR MEASURING BLOOD OXYGEN SATURATION

[75] Inventor: Stanley O. Heinemann, Irvine, Calif.

[73] Assignee: Bentley Laboratories, Irvine, Calif.

[21] Appl. No.: 236,941

[22] Filed: Feb. 27, 1981

[51] Int. Cl.³ .................. G01N 21/27; G01N 33/48
[52] U.S. Cl. ............................. 356/41; 250/214 AG; 356/409
[58] Field of Search .................. 356/39–42, 356/408–411, 370, 445, 434–435, 432, 448, 319, 321–325, 402–407, 412–425; 250/205, 578, 214 C, 214 AG, 565

[56] References Cited

U.S. PATENT DOCUMENTS

| | | | |
|---|---|---|---|
| 1,572,160 | 2/1926 | Robbins | 356/432 |
| 3,069,013 | 12/1962 | Neubrech et al. | 356/407 |
| 3,330,904 | 7/1967 | Gebel | 356/405 |
| 3,676,005 | 7/1972 | Chance | 356/320 |
| 3,730,627 | 5/1973 | Kent | 356/408 |
| 3,799,672 | 3/1974 | Vurek | 356/41 |
| 3,807,875 | 4/1974 | Fischer et al. | 250/578 |
| 3,847,483 | 11/1974 | Shaw et al. | 356/41 |
| 3,854,878 | 12/1974 | Kiesow | 356/41 |
| 3,902,806 | 9/1975 | Bober | 356/41 |
| 4,208,578 | 6/1980 | McLoughlin et al. | 250/214 AG |
| 4,297,587 | 10/1981 | Baker | 250/214 AG |

OTHER PUBLICATIONS

Takatani et al., "A Noninvasive Tissue Reflectance Oximeter", Ann. of Biomed. Eng., vol. 8, #1, 1980, pp. 1-15.
Korlev et al., "An Attachment Based on the Method of Disrupted Total Internal Reflection with Partial Compensation of the Variation in the Penetration Depth of the Light Flux," Instru. & Experimental Techniques, vol. 18, #5, Sep.-Oct. 1975, pp. 1562-1564.

*Primary Examiner*—William H. Punter
*Attorney, Agent, or Firm*—Lyon & Lyon

[57] ABSTRACT

A device and method for measuring blood characteristics and parameters, especially arterial, venous, or differential blood oxygen saturation levels uses one or two probes containing a unique configuration of light emitters of two different wavelengths, and sensors which alternately illuminate and read reflected light from blood passing through a specially-designed cuvette. Electronic comparison of reflected radiation received by the probes produces a voltage which is linearly related to blood oxygen saturation level. An opto-electronic feedback network compensates for differences in blood optical density.

33 Claims, 8 Drawing Figures

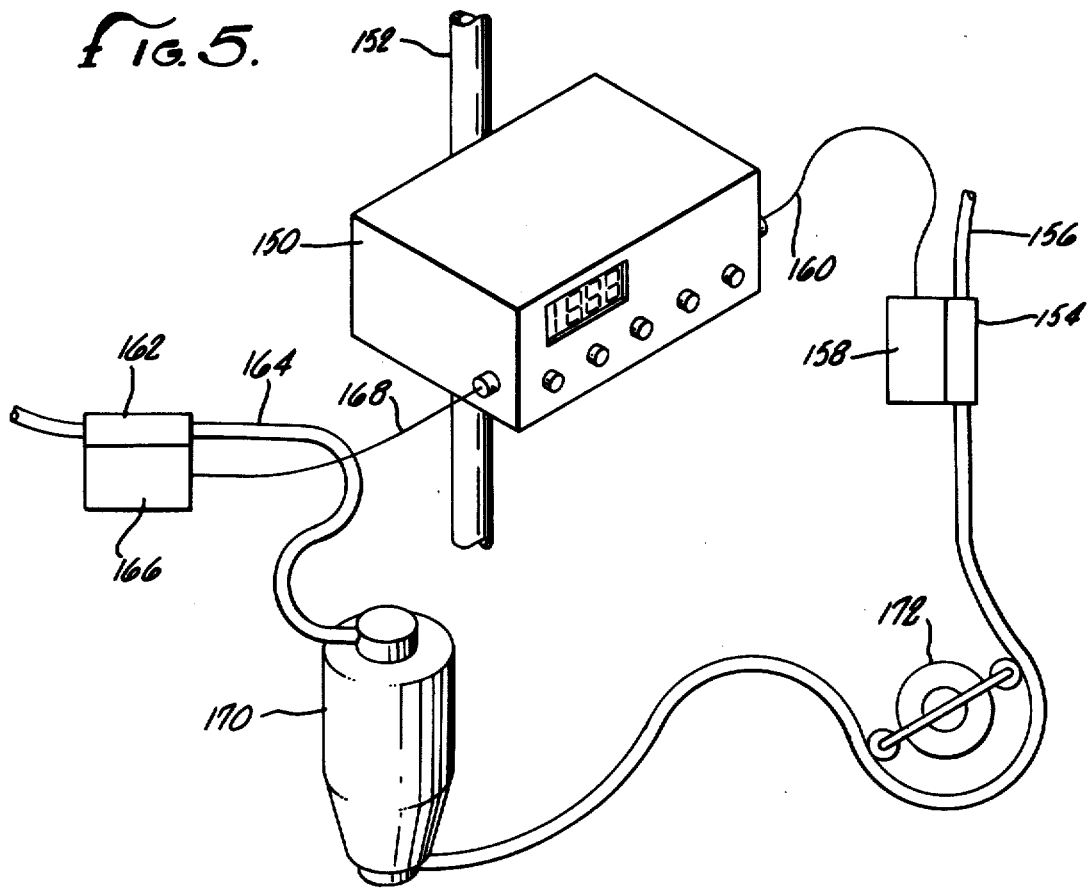
FIG. 5.
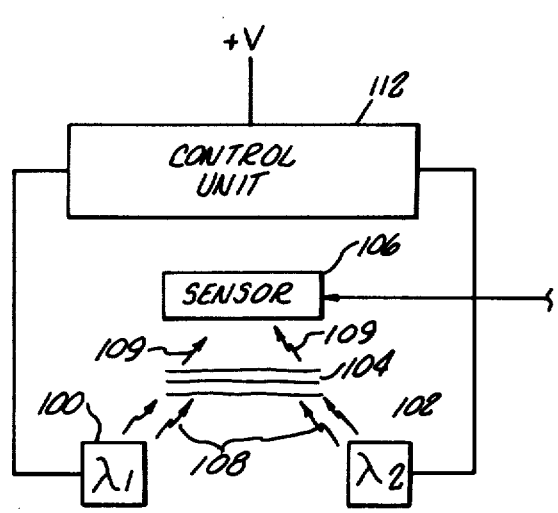
FIG. 2B.
FIG. 7.

APPARATUS AND METHOD FOR MEASURING BLOOD OXYGEN SATURATION

BACKGROUND OF THE INVENTION

It is well known that blood oxygen saturation can be measured optically. Devices for performing such measurement, known as oximeters, exist in the prior art; e.g., U.S. Pat. No. 3,799,672 to Vurek; U.S. Pat. No. 3,638,640 to Shaw.

The advantages of optical measurement of blood oxygen saturation levels during procedures, such as cardiopulmonary bypass during open heart surgery, are apparent. Utilization of extracorporeal blood circulation during such procedures facilitates optical monitoring of blood oxygen saturation and obviates the need for invasive withdrawal of samples for descrete measurements which aggravate blood loss and increase the risk of infection.

The prior art devices for optically measuring blood oxygen saturation levels by utilizing infra-red and red radiation, principally in the 6600 and 9000 Angstrom wavelength ranges, respectively, have constituted an advance in the art over single light source devices.

However, many of such devices cannot be adjusted to compensate for hematocrit fluctuations, with the result that readings are somewhat inconsistent among blood samples containing different hematocrit levels. Other devices can be manually adjusted to compensate for variations in hematocratic levels by varying the current to the light sources. This often results in non-uniformity of photon penetration depth into the blood sample, with less than optimum results. For instance, as a result of the inability of such a device to compensate for varying hematocrit levels, several things may occur. If the hematocrit level is low, the light tends to be transmitted through the blood, which is not optically dense, and reflected off the back wall of the cuvette from which it is transmitted via the blood to the light sensor, thus causing an erroneous reading. If the hematocrit level is comparatively high, the blood is optically dense and the light tends to reflect from the blood's surface, giving rise to error due to surface effects. In addition, the higher optical density of blood at higher hematocrit levels results in a lower amount of reflected light transmitted to the sensor, causing a relatively poor signal to noise ratio at the transducer level, which effect is multiplied by the signal processing and contributes significantly to error.

In addition, the accuracies of the prior art devices are limited by flow-direction, turbulence and microemboli effects, as well as by the efficiency of the optical coupling between the light sources, cuvette walls and photosensors.

Finally, some of the prior art devices are subject to error through the introduction of noise from various sources into the electronic circuitry which derives blood oxygen level readings from the reflected light energy.

SUMMARY OF THE INVENTION

The present invention is an advancement in the art of optical blood oxygen saturation meters, and overcomes many of the inadequacies and shortcomings of prior similar devices by its unique combination of novel features.

First a specially-designed cuvette, through which blood flows as it is being monitored, is provided examine the blood over a relatively large surface area. It enables a good average reflective signal to be obtained by permitting location of the light emitters and sensor as close to the blood path as possible, and avoids interjecting unpredectable surfaces which distort the optical feedback path. The cuvette is provided with a flat surface as a window in order to enable most of the generated and refleted photons to penetrate the cuvette wall perpendicular to the surface of the window. Use of a flat window with a relatively large surface area also minimizes internal surface contamination effects because the light is allowed to penetrate the blood sample to a controlled depth rather than reflecting from a point on the surface. A substantially straight flow through path minimizes turbulence, hemolysis, and cavitation effects.

Second, the present invention employs a novel sensor head design which avoids flow direction and microemboli interference by employing a plurality of light sources for each wavelength of light used. This also has the effect of increasing the signal level, and hence, the signal to noise ratio, and lessens interference caused by ambient room light. Geometric layout of light sources and sensor provides optimum light penetration, minimum stray surface reflection, and good dynamic signal levels over wide hematocrit changes.

Third, a novel circuit is provided which employs optical feedback, not only to match the light output of the two different wavelength light sources, but to set the absolute level of light reflected back from the blood to the sensor to compensate for wide variations of hematocrit levels by assuring uniform depth of penetration of light into the blood being sampled. The circuit also compensates for temperature variations and component tolerances, uses pulse multiplying and integrating techniques to reduce the effects of alternating current capacitively coupled noise and external light-induced signals. In addition, providing a higher intensity light source for a short period of time further improves the signal-to-noise ratio and allows sustained battery power operation, thus improviing patient safety by reducing shock hazard.

BRIEF DESCRIPTION OF THE DRAWINGS

FIG. 2b is a portion of the block diagram of FIG. 2a showing radiation transmitted to a sensor through a blood sample.

FIG. 5 shows the complete system of the preferred embodiment of the instant invention, set up to measure arterial or venous blood oxygen saturation levels.

FIG. 7 is a diagrammatic view of the preferred sensor head of the instant invention.

GENERAL DESCRIPTION

Although the present invention finds its principal use in the medical field, particularly in the measurement of blood oxygen saturation, it may be satisfactorily applied to the measurement of other physical phenomena which exhibit similar behavior and meet the criteria to be developed herein. Blood oxygen saturation measurement, the preferred embodiment, will be used as an illustrative example. As used herein, the word blood includes natural and synthetic blood, and both human and animal blood.

Figure 1:
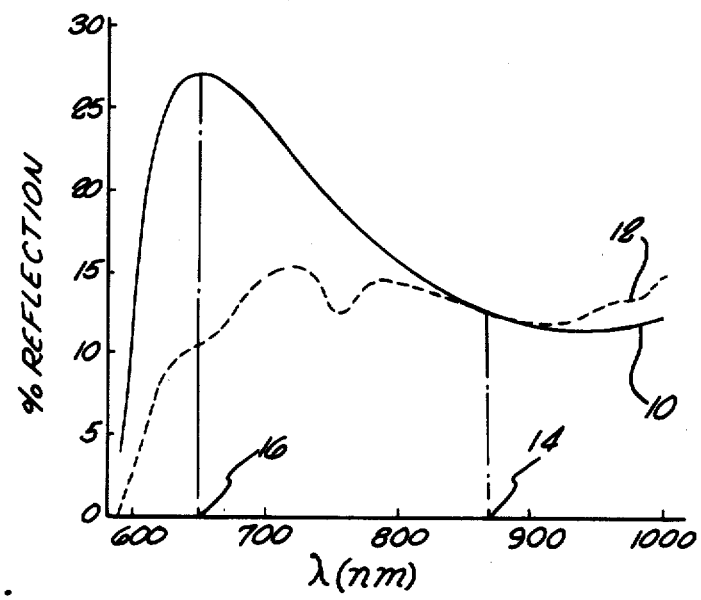
FIG. 1 is a graph depicting the percent reflection of light from ox blood as a function of light wavelength.

Referring first to FIG. 1, the curve representing the reflectivity of oxyhemoglobin as a function of wavelength is indicated by the numeral 10 on FIG. 1; the curve representing reflectivity of deoxyhemoglobin as a function of wavelength is indicated by numeral 12. It will be seen that the reflectivity of oxyhemoglobin (100% saturated blood) varies with the wavelength of incident radiation. Deoxyhemoglobin (unoxygenated or 0% saturated or unsaturated blood) also varies in reflectivity with the wavelength of incident radiation, but the two functions are distinctly different.

It will be noted that at point 14 on the axis, representing a particular wavelength, the reflectivity of both oxygenated and deoxygenated hemoglobin is equal. This point is called the isobestic point. The wavelength at which it occurs is chosen as one point of reference for measurement. While variation in the hematocrit level of blood will affect its absolute reflectivity, such variation has been emperically determined to have relatively the same effect on reflectivity at the isobestic point regardless of the oxygen saturation level of blood being measured. Thus, the isobestic point remains the same for wide variations in hematocrit levels and is a satisfactory reference point.

At a point indicated by numeral 16 on the axis of FIG. 1, representing a second wavelength, the difference between reflectivity of oxyhemoglobin and deoxyhemoglobin is at a maximum. The wavelength at which this maximum difference occurs is chosen as the other point of reference for measurement. While other points at which blood exhibits a change in reflectivity with differing oxygen content could also be used successfully, point 16 is chosen because the maximum difference appearing there will produce the greatest difference in reflectivity for all oxygen saturation levels, thus providing a better signal to noise ratio for all measurements. This will improve measurement accuracy, especially at low reflectivity levels. Although FIG. 1 was made using ox blood, points 14 and 16 do not differ appreciably for natural human blood; these points may differ for synthetic human blood and other animal blood but can be easily ascertained by those skilled in the art using known methods.

Changes in blood oxygen saturation level and changes in reflectivity caused thereby exhibit a linear relationship to one another, hence any transfer function which relates them together will also be linear. In encountering changes in other blood properties and parameters which are characterized by changes in reflectivity, it is apparent that the application of this technique to such phenomena is possible if the relationship between the change in reflectivity and the change in property or parameter causing it is either linear, logarithmic, exponential, or indeed any function which may be faithfully reproduced or simulated electronically, and the following additional criteria are met. The change in reflectivity must have an isobestic point and must also have a point of maximum or at least appreciable difference. The wavelengths associated with these points must be sufficiently separate so that the spectral bandwidths of radiation emitters utilized to measure the absolute reflectivity are mutually exclusive. In addition, as already mentioned, the relationship between the change in reflectivity and the change in parameter must be capable of electronic simulation.

GENERAL DESCRIPTION OF THE INVENTION

Figure 2A:
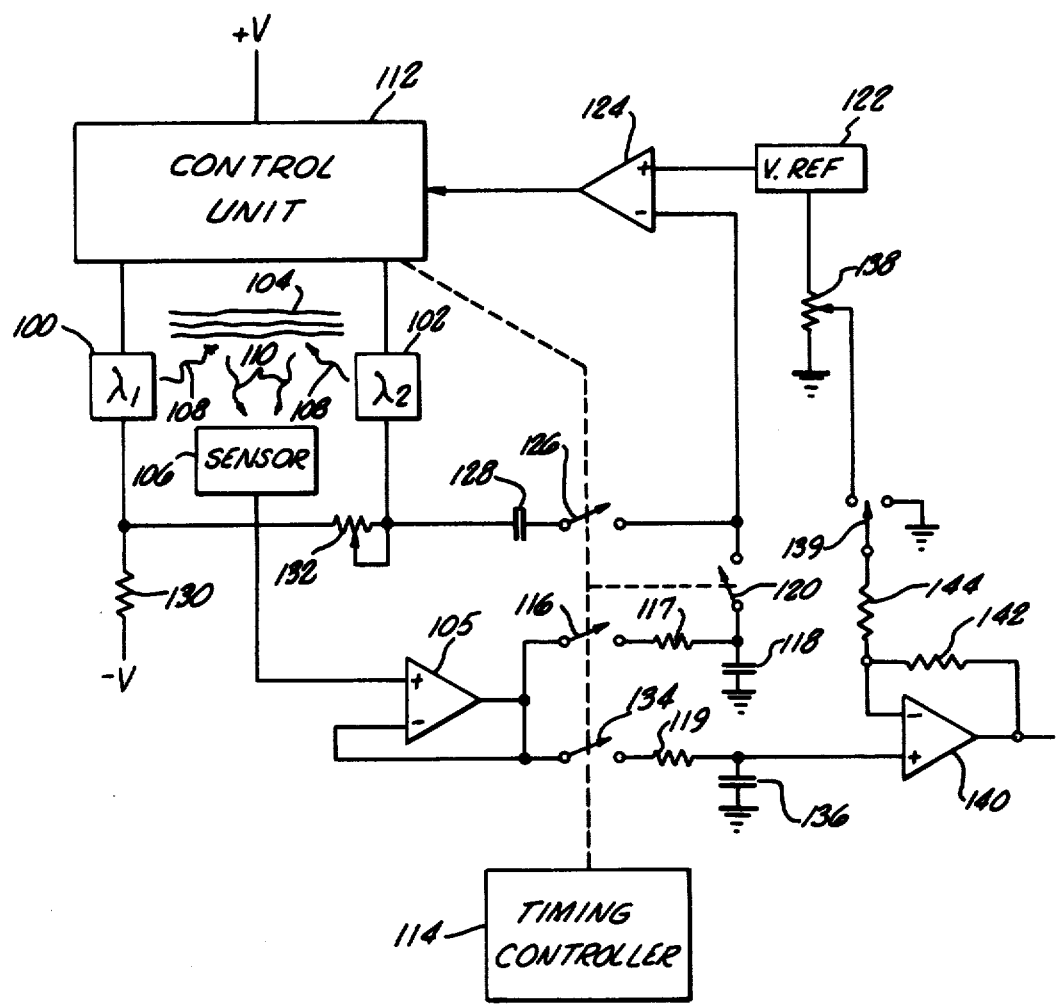
FIG. 2a is a block diagram of apparatus which operates according to the instant invention and showing radiation reflected to a sensor from a blood sample.

Operation of the present invention can best be understood with reference to FIG. 2a. Radiation sources 100 and 102 of two different wavelengths λ1 and λ2, and which are capable of being selectively and adjustably energized, are positioned proximately to a sample 104 which is to be examined. A radiation sensor 106, having a relatively flat bandwidth response which encompasses wavelengths λ1 and λ2, is proximately placed near sample 104 so as to receive radiation reflected from or transmitted through sample 104. Although FIG. 2a diagrammatically represents incident radiant energy 108 and reflected radiant energy 110, it will be apparent to those skilled in the art that radiation sensor 106 could alternately be placed such that it could receive radiant energy transmitted through sample 104.

It will be appreciated by those skilled in the art that radiation sources 100, 102 comprise radiation emitters of narrow bandwidth. Such sources include, but are not limited to, lasers, light emitting diodes (LEDs), or other light sources, such as incandescent or gas vapor lamps, equipped with filters. The amount of radiant energy that such sources emit must be controllable, either by electrical or electronic means, or by optical means such as neutral density filters or the like, or by other means.

Control unit 112 is shown connected to radiation sources 100, 102; it can energize or deenergize them and can control the amount of radiation emitted. While the disclosure herein refers for convenience to light sources controlled by means of electrical current, other modes of control for other transducers will readily suggest themselves to those skilled in the art.

The intensity of radiation sources 100, 102 is controlled in the present invention by optical feedback. Two forms of opto-electronic feedback are used; control of the level of radiation transmitted by or reflected from sample 104 by radiation source 100, and relative control of radiation source 102, i.e., controlling the output level of radiation source 102 by reference to the output level of radiation source 100. It will be appreciated that the relative roles of controlled or controlling sources may be reversed as required by particular applications without departing from the spirit of the invention.

The first feedback loop, which controls the level of radiation transmitted by or reflected from sample 104 by radiation source 100 is a new concept applied to these measurement techniques. In measuring changes in reflection or transmission of radiation as a function of changes in blood parameters, as well as in other measurement techniques, it is desirable to maintain a constant signal-to-noise ratio when making measurements across a wide range of transmission or reflectance values. The quality of any measurement technique is limited by the dynamic range over which accurate measurements can be made. In the case of measuring phenomenon which exhibit a region of isobestic behavior and which are susceptible to measurement by the dual wavelength technique, I have discovered that by maintaining a constant level of reflected or transmitted energy received by a radiation sensor an acceptable signal-to-noise ratio may be maintained over a wide dynamic range.

The first feedback loop of the present invention is defined as follows. Radiation sensor 106 senses radiation reflected from or transmitted through the sample 104 when timing control unit 114 activates radiation source 100 through control unit 112. The output of radiation sensor 106 is a voltage, or a current which may be expressed as a voltage by passing it through a resistor (not shown). The signal from radiation sensor 106 is amplified and/or buffered by amplifier 115 as needed. FIG. 2a shows amplifier 105 configured as a source follower. Timing control unit 114 closes switch 116 simultaneously upon activating radiation source 100. The voltage output of radiation sensor 106 is stored in storage device 118 after passing through switch 116. Although storage device 118 is shown in FIG. 2a as a capacitor, it is well understood that other means, including but not limited to, digital memory means storing digital (binary) representation of voltage may be employed. In this respect, it will be appreciated by those skilled in the art that use of storage devices other than capacitors will eliminate the need for charging resistors 117 and 119.

Switch 120 closes along with switch 116 when radiation source 100 is energized, also under the control of timing control unit 114. The voltage on storage unit 118 is compared with a reference voltage 122 by amplifier 124, which generates an amplified error signal which is fed to control unit 112. Reference voltage 122 is set to define a level of reflected or transmitted radiation in order to maintain an acceptable signal-to-noise ratio for the system. This error signal, fed to control unit 112 by amplifier 124, causes control unit 112 to adjust the radiation output of radiation source 100 in order to maintain the proper desired level of transmitted or reflected radiation received by radiation sensor 106 and thus sets the level of photon penetration depth into the blood sample. This is accomplished by varying the voltage which controls the current to radiation sources 100 and 102.

Timing control unit 114 also closes switch 126 during the time radiation source 100 is activated. This causes storage unit 128 to store a voltage which is the difference between the voltage on storage unit 118 and the voltage across resistor 130 which is connected in series with radiation source 100. Since the current which passes through radiation source 100 must also pass through resistor 130, the voltage developed across resistor 130 is proportional to the current driving radiation source 100. Therefore, the voltage stored in storage device 128 will be proportional to the current used to drive radiation source 100. Variable resistor 132, interposed between storage device 128 and resistor 130, may be used to establish a ratio between the current needed to drive radiation source 100 and that needed to drive radiation source 102 in order to compensate for differences in radiation output per unit current between the two radiation sources. It is to be noted that storage device 128 may optionally have one of its terminals connected to the common voltage supply and have the other one of its terminals connected through switch 126 to either the junction of radiation source 100 and resistor 130 or the junction of radiation source 102 and variable resistor 132. Either of these connections (not shown) will also cause a voltage proportional to the drive current for radiation source 100, either scaled or unscaled, to be stored in storage device 128.

The second feedback loop is defined as follows. Timing controller 114 causes control unit 112 to activate radiation source 102. In the operation of this feedback loop, switch 126 is closed and switch 134 is also closed. The closure of switch 126 causes the voltage stored in storage unit 128 to appear on the inverting input of amplifier 124, which compares this voltage with reference voltage 122 and produces an amplified error voltage at its output which causes control unit 112 to adjust the current flowing through radiation source 102 in order that its radiant output may track that of radiation source 100. In alternate embodiments (not illustrated) where storage device 128 and switch 126 are connected in the alternative configurations discussed above, an extra switch (not shown) is needed to place the voltage across storage device 128 on the non-inverting input of amplifier 124. Where storage device 128 is a capacitor in these embodiments, it should be provided with a charging resistor like resistors 117 and 119. The reflected or transmitted radiation received by radiation sensor 106 passes through closed switch 134 and is stored in storage device 136.

The voltages stored in storage devices 118 and 136 are proportional to the radiation transmitted through or reflected from sample 104 and received by sensor 106 at wave lengths $\lambda_1$ and $\lambda_2$, respectively. These voltages may be combined electronically to measure the desired parameter. In fact, the voltage stored in storage unit 136 is proportional to the ratio of the two reflectances or transmissibilities. The mathematical relationship between this ratio and percent blood oxyen saturation is well understood by those skilled in the art.

Measurement of blood oxygen saturation levels is instructive as an illustration of the present invention. In this example, radiation source 100 is a light source having a wavelength equal to that indicated at numeral 16 of FIG. 1, the point of maximum difference between oxyhemoglobin and deoxyhemoglobin reflectance. Radiation source 102 is a light source having a wavelength equal to that indicated at numeral 14 of FIG. 1, representing the isobestic point of reflection of oxy and deoxyhemoglobin. In this case radiation sensor 106 will be a light sensor, such as a phototransistor, having a substantially flat bandwidth response encompassing these two wavelengths.

Light sources 100 and 102, and sensor 106 are positioned to irradiate and receive reflected radiation, respectively, from a blood sample placed in a good optical coupling relationship with said light sources and sensor. It will be understood by those skilled in the art that transmission as well as reflection phenomena may be utilized in this procedure. The operation of this embodiment proceeds as described above. When the procedure is completed, storage device 136 will have across it a voltage representative of a blood oxygen saturation level which must be compared with a voltage representing a 100% blood oxygen saturation level. Such a reference voltage is developed across potentiometer 138. The comparison is made by operational amplifier 140. It is within the capacity of those skilled in the art to choose feedback and input resistors 142 and 144 respectively such that convenient voltage levels represent the differing levels of blood oxygen saturation, e.g., zero volts can represent an oxygen saturation level of 0% and 10 volts can represent an oxygen saturation level of 100%. When a gain structure producing such voltage outputs is used, the voltage outputs are directly translatable to blood oxygen saturation level percentages.

In other applications where a reference voltage is not needed, switch 139 is switched to the common voltage terminal (ground), and amplifier 140 may be used a buffer or gain stage as is well understood in the art.

In a system such as this, it is preferable to have timing controller 114 activate the various radiation sources and switches alternately, with a relatively small duty cycle. Storage devices 118 and 136 may be capacitors which can then integrate the voltage pulses received, thereby achieving a greater signal to noise ratio. In addition, pulsed operation keeps the light sources from generating excessive heat, which could tend to cause hemolysis of the blood under study. Generation of excessive heat could also tend to destroy the linearity of the current-to-photon transfer characteristic of the light sources and introduce inaccuracy.

Referring now to FIG. 2b, an alternate embodiment of the system shown in block diagram of FIG. 2a, utilizing transmitted radiation is shown. Incident radiant energy 108 from radiation sources 100 and 102 passes through blood sample 104 and is shown as transmitted radiant energy 109 which is received by sensor 106. The resultant signal is then processed as described with reference to FIG. 2a.

The best mode of practicing the present invention as it relates to measurement of blood oxygen saturation involves placing a sensor head containing red and infrared light sources and a photosensor in optical contact with the blood to be examined, alternately irradiating the blood with short pulses of red and infra-red light, detecting the reflection of that light from the blood by the photosensor, and using signals developed from the reflective light to determine the oxygen saturation level. This mode is particularly adapted to examination of extracorporeally circulating blood, although it works equally well with isolated, drawn blood samples. Satisfactory optical coupling between the blood to be examined and the light sources and photosensor may be achieved directly or by means if fibre optics elements, as will be apparent to those skilled in the art.

A disposable cuvette is preferably used to hold the blood being examined. Such a cuvette is illustrated in FIGS. 3 and 4 and will be discussed in detail.

Figure 3:
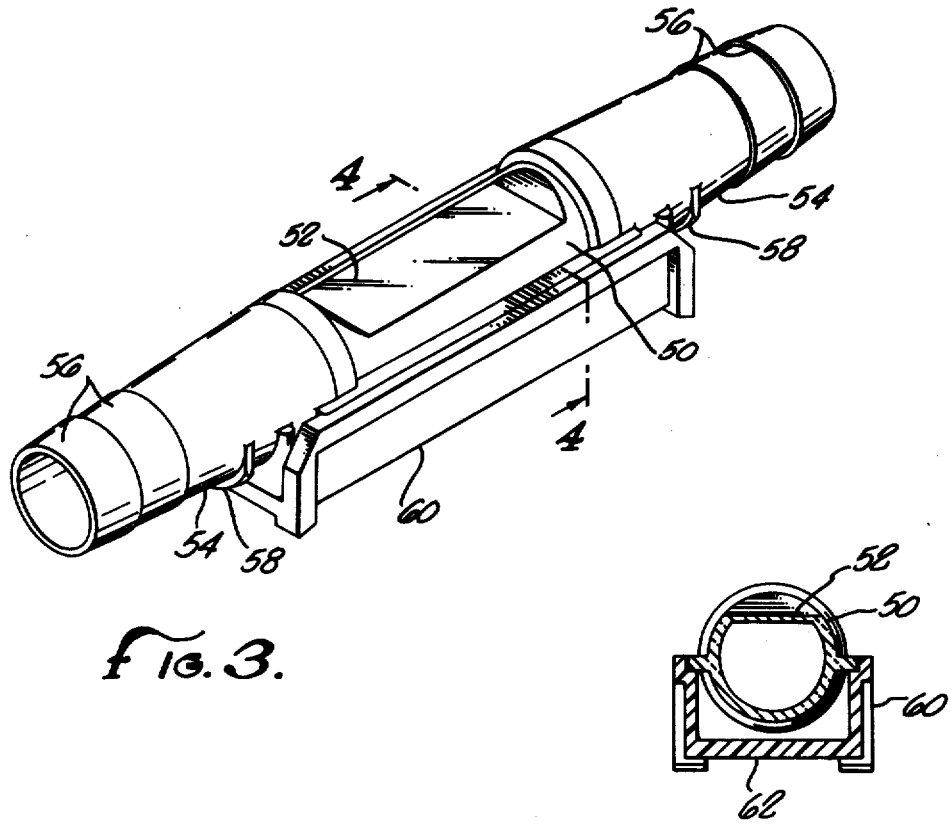
FIG. 3 is a cuvette used in the apparatus of the instant invention.

Referring now to FIG. 3, a cuvette is shown having an optically clear body portion 50. A substantially flat window portion 52 is disposed in the body portion and has its largest dimension in the direction of blood flow. The end portions 54 of the cuvette are provided with barbs 56 to hold securely in place tubing which is to be connected to the cuvette when it is in use and stops such as 58 for such tubing may be provided if desired.

The cuvette is carried in a plastic frame 60, which is shaped to provide easy insertion of and a snug fit for the cuvette when it is placed in a holder which will contain a sensor head assembly to be brought in optical contact with window 52. Frame member 60 aids in assuring consistency of measurement results from cuvette to cuvette by establishing a positional relationship between the window 52 of the cuvette and the sensor head with which it is to be used.

Figure 4:
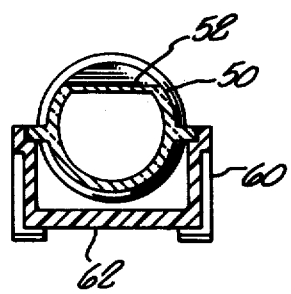
FIG. 4 is a sectional view of the cuvette of FIG. 3, taken along lines 4—4.

Referring now to FIG. 4, the frame portion 60 of the cuvette is equipped with an opaque non-reflective portion 62 which is disposed behind the window of the cuvette. This opaque non-reflecting portion of the frame serves to reduce any reflection from the back walls of the cuvette when light radiation of sufficient intensity to penetrate through the blood flowing in the cuvette is presented at the window. Its use will tend to reduce the possibility for erroneous readings caused by reflection of light from the back walls of the cuvette through the blood and back to the photosensor.

A flat surface was chosen as a window in order to enable most of the reflected photons to penetrate perpendicularly to that window. The window allows examination of the blood over a relatively large surface area. A good average reflective signal is obtained by locating the light sources and photosensor as close to the blood path as possible, and without interjecting unpredictable surfaces which may distort the optical feedback. An optically clear window at the required wavelengths was also chosen so that the variable optical density of any intermediate medium will not affect the response, thus enabling repeatable signals to be obtained between different cuvettes. Lexan 111, manufactured by the General Electric Co. has such properties and is suitable for use in the present invention.

The large flat window of the cuvette also minimizes internal surface contamination effects because the light penetrates deeply into the sample rather than reflecting from a point on the surface. A preferred depth of light penetration is about 3 millimeters. The cuvette is designed to clip securely into a holder which does not allow rotational or longitudinal movement. This almost eliminates effects caused by mechanical movement and positioning. Such a holder also serves to maintain constant and sufficient optical coupling between the cuvette window and the sensor head containing the light sources and photosensor and preferably houses the circuitry associated with the sensor head. The cuvette is designed to have straight flow-through characteristics to minimize or eliminate turbulence, hemolysis, and cavitation. It should be completely transparent from the sides to permit priming inspection. The depth of the viewing area should be choosen to minimize light reflection from the opposite surface, and external light source interference. The cuvette is preferably covered with a light-proof backing which is black on the inside, to further reduce unwanted reflection.

The length and shape of the cuvette should also be chosen to attenuate any ambient room light which may be conducted along the blood or cuvette wall into the viewing area.

It is also preferable that the holder into which the cuvette is designed to clip securely contain the circuitry associated with the sensor head as well as the sensor head itself. The power leads and timing signals, as well as the output connection for the circuit, can be provided by use of a small flexible cable attached at one end to the cuvette holder and at the other end to a chassis housing the power supply, timing circuits, and display. Battery power is preferred as a power source because reduces the risk of shock to the patient, even though the only coupling between the measuring system and the blood is optical coupling.

An arrangement for measuring blood oxygen saturation of venous and arterial blood during a typical surgical procedure requiring extracorporeal oxygenation of the blood is depicted in FIG. 5. The main chassis 150, housing the power supply, display and display circuitry, switch and switching circuitry, and timing circuitry is shown mounted on an IV pole 152 for convenience.

Arterial cuvette 154 is shown connected to arterial blood flow line 156. Arterial cuvette housing 158 is mountingly affixed to arterial cuvette 154; it is connected also to main chassis 150 by a cable 160 which carries the various power, output, and timing signals. Similarly, venous cuvette 162 is shown connected to venous flow line 164. Venous cuvette holder 166 is shown mountingly affixed to venous cuvette 162 and communicates with main chassis 150 via cable 168. Extracorporeally circulating blood in arterial and venous lines 156 and 164, respectively, is oxygenated by oxygenator 170 and pumped through the patient's system by pump 172.

The circuitry contained in arterial and venous cuvette holders 158 and 166 respectively, is identical. One of such circuits is depicted in and will now be discussed with reference to FIG. 6.

Figure 6:
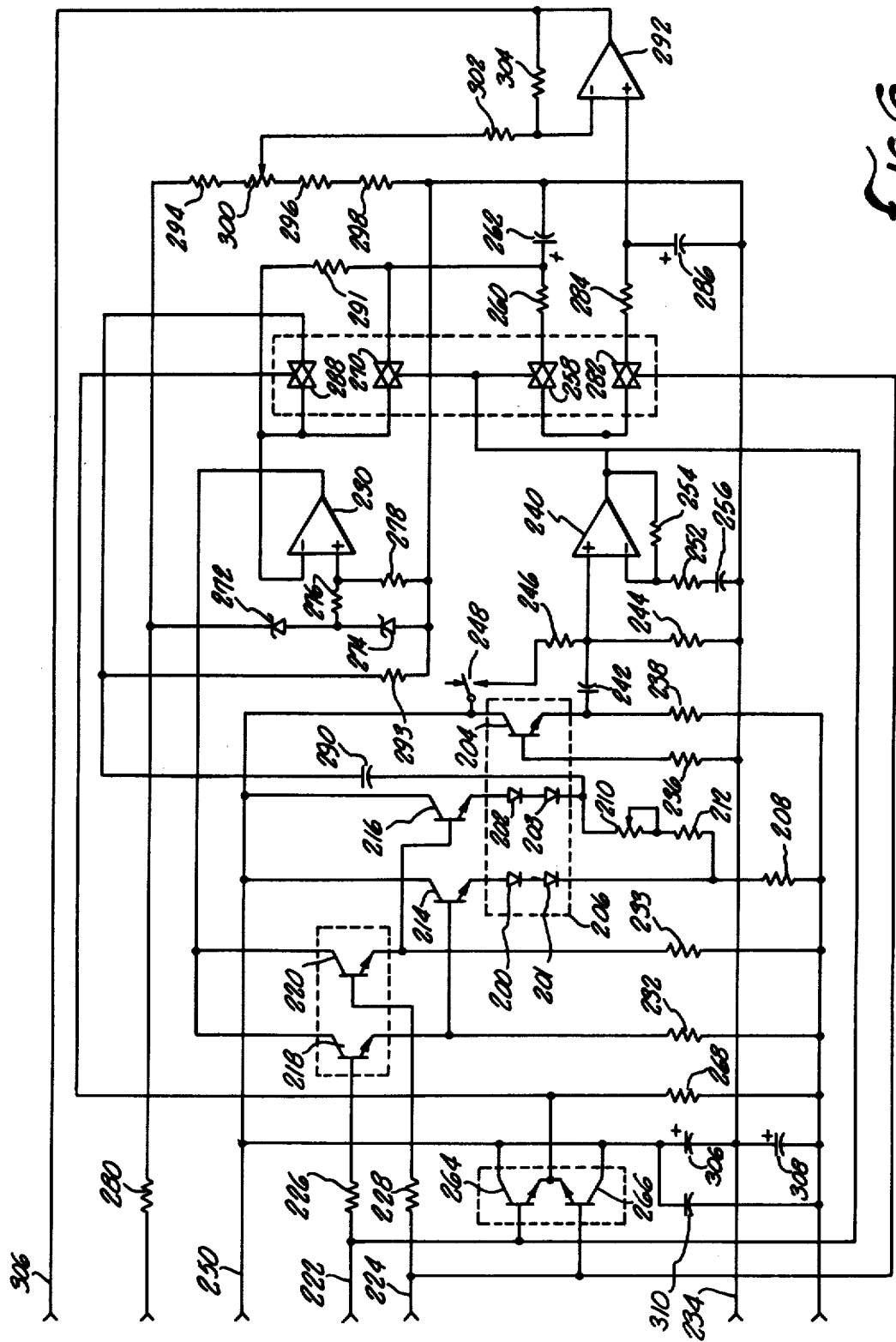
FIG. 6 is a detailed schematic diagram of the circuitry associated with the sensor head of the present invention which is preferably housed in the same location as the sensor head.

Light emitting diodes (LEDs) are used as light sources for both the red and infra-red wavelengths in the circuit of FIG. 6. They provide a substantially narrow band emission at their rated wavelengths. LEDs also have a photon output which leaves a linear relationship to the current passing through them, which makes them suitable candidates for precision control of light output by controlling the current producing that output. The two red LEDs 200, 201 have a wavelength of 6600 Angstroms. LEDs designated MV-50, made by Monsanto, are suitable for use as red light sources in the present invention. Two infra-red LEDs 202, 203 have a wavelength of 9000 Angstroms. LEDs designated ME-60, also made by Monsanto, are suitable for use as infra-red light sources in the present invention.

Phototransistor 204 is used as a light sensor in the preferred embodiment. To be satisfactory for use in the present invention, a phototransistor should possess the following characteristics: its spectral bandwidth response should be relatively flat over the range emcompassing the two light wavelengths used and should be such that any small drift in the emitted wavelength and/or sensor will cause the sensitivity to drift in the same direction for both wavelengths of light emission; it should have a flat lens so that it may be placed in as close contact as possible with the window surface of the cuvette containing the blood being examined; and it should have a fairly wide angular response characteristic. Phototransistor FPT 110B, manufactured by Fairchild Semiconductor Co. is one sensor suitable for use in the present invention.

Together, LEDs 200, 201, 202, and 203, and phototransistor 204 make up the sensor head of the preferred embodiment. The sensor head is indicated by the numeral 206. The layout of the sensor head 206 is shown in FIG. 7. The placement of the components of the sensor head was chosen to avoid flow-direction, microemboli and other particle interference of the reflected photons. A large area of exposure is preferably selected, including a symmetrical pattern of light emitters which appears the same in either direction of flow. This arrangement, which includes the use of two light emitters per wavelength, also increases the signal level, and, hence, the signal-to-noise ratio, thus reducing noise problems, and reduces the effects of interference from ambient room light.

Spacing of the light emitters 200, 201, 202, and 203 from the phototransistor sensor 204 should preferably be optimized to give the best depth of light penetration,, minimum stray surface reflection, and good dynamic signal levels over a wide range of hematocrit changes.

In the preferred embodiment, FIG. 7 shows the relative spacing of the sensor head elements. The two sets of LED's 200, 203 and 201, 202 will be spaced approximately 5 millimeters on either side from the center of the lens of the phototransistor 204 on an axis in the direction of blood flow, and touch one another on an axis transverse to the blood flow direction when the sensor head is brought into contact with a cuvette. LEDs of like wavelength are located diagonally from one another. While this configuration has been found to provide optimum performance, any arrangement which satisfies the above criterion will give good results and is within the scope of the present invention. A good arrangement would be to have the different wavelength LEDs manufactured in the same package so that they would better aproximate a point source and emit radiation through the same lens.

Additionally, as illustrated in FIG. 7, a fiber optic link may be used to optically couple the radiation sources 200–203 and sensor 204. A fiber optic cable bundle (dashed lines), consisting of a separate portion 192a–c for each source or sensor, couples radiation to and from the blood sample 104 flowing in a cuvette represented by flat surface 190. For illustration fiber optic cable portion 192a and 192b couples radiation from radiation sources 200 and 202 to the surface 190 of the cuvette. Reflected radiation is coupled via fiber optic cable portion 192c to sensor 204.

Referring again to FIG. 6, red LEDs 200 and 201 are connected in series with one another and with resistor 208. The other end of resistor 208 is returned to the negative supply voltage line 209.

The infra-red LEDs 202 and 203 are also connected in series with one another and in turn are connected in series with variable resistor 210 and fixed resistor 212. Variable resistor 210 is preferably a multi-turn potentiometer. Resistors 210 and 212 equalize the light output of the red LEDs 200 and 201 and the infra-red LEDs 202 and 203. Because the infra-red LEDs 202 and 203 are more efficient in current-to-photon transfer, resistors 210 and 212 compensate to assure that the red LEDs 200 and 201 and the infra-red LEDs 202 and 203 produce the same photon output when energized. This equalization is accomplished by adjusting the value of resistor 210.

LEDs 200, 201, 202 and 203 are energized by NPN transistors 214 and 216 respectively. JEDEC 2N2222 transistors or their equivalents are satisfactory for this purpose. Transistors 214 and 216 are selectively energized by NPN transistors 218 and 220, respectively, by providing a voltage pulse of sufficient magnitude at points 222 and 224, respectively, to cause base current through resistors 226 and 228, respectively, of sufficient magnitude to saturate transistors 218 and 220.

Transistors 218 and 220 are configured as emitter switches, which are known to be more efficient than collector switches. In emitter switch mode, the bases of transistors 214 and 216, follow the collectors of transistors 218 and 220, which in turn follow the output LED emission control amplifier 230.

LED emission control amplifier 230 sets the level of emission of the red LEDs 200 and 201 by controlling their drive current via transistors 214 and 218. It also functions to control the emission level of infra-red LEDs 202 and 203 by causing their drive current to track that of red LEDs 200 and 201 via transistors 216 and 218. It, as well as all other amplifiers used in the preferred embodiment, is an operational amplifier characterized by a high slew rate, low input leakage and bias current, low differential offset and offset drift, and low quiescent supply current. Texas Instruments TL 060 series amplifiers are suited for this application.

The blood oxygen saturation measurement process is carried out by alternately providing pulses to points 222 and 224 to energize LEDs 200, 201, 202 and 203, respectively. Details concerning the generation of such pulses are well known in the art and are accomplished via well-understood design principles using digital integrated circuit building blocks. For present purposes it is sufficient to note that pulses of sufficient amplitude to saturate transistors 218 and 220 may be approximately 210 microseconds in duration and may be spaced apart by rest periods of approximately 21 milliseconds, resulting in a duty cycle of 1%. Preferably, the pulse repetition rate should be a non-multiple of both 50 and 60 Hz to avoid beat frequency effects with alternating current power sources, since interference from those sources can be optically or electrically coupled into the apparatus.

A red shine cycle is initiated first. A pulse appears at point 222 and, through resistor 226, causes transistor 218 to saturate, thus providing a voltage across resistor 232, which acts to imporive the fall time of the switching pulse. Resistor 233 performs the same function for transistor 220. This voltage is equal to the voltage at the output of LED emission control amplifier 230, less the collector-emitter drop of saturated transistor 218. The current flowing into the base of transistor 214 is thus controlled by the output of LED emission control amplifier 230 and causes a current pulse of 210 microseconds in duration to energize red LEDs 200 and 201. The light pulse from LEDs 200 and 201 penetrates into the blood being monitored. A portion of this light energy is reflected back and is received by phototransistor 204, which is configured in common collector mode. The base of phototransistor 204 is connected to the ground or common line 234 through resistor 236, which serves to improve its rise time. Current flowing through phototransistor 204 produces a voltage pulse across resistor 238, whose magnitude is proportional to the reflected light received. This pulse appears on the non-inverting input of amplifier 240, through an RC network comprising capacitor 242 and resistor 244. This network acts as a high pass filter to reject 50- and 60-cycle noise components present due to inductive coupling and introduction through alternating current ambient room lighting. Resistor 246 and switch 248 together act as a safety mechanism to assure that the cuvette in the blood path is correctly seated in the probe assembly. Until the cuvette is properly inserted and aligned in the probe assembly containing the sensor head, switch 248 causes resistor 246 to act as a pull-up resistor to positive supply voltage line 250. This will result in a clearly observable gross error in reading, e.g. −1% saturation, until corrected. Resistors 252 and 254 are chosen to give amplifier 240 a gain of 21 to give a correctly scaled reading at the output. Further, resistor 252 and capacitor 256 to limit the DC offset and drift of amplifier 240; without them, these parameters would be amplified by the gain of amplifier 240 and introduce significant error into the system.

The output of amplifier 240 is connected, through CMOS analog switch 258, to resistor 260 and red-store capacitor 262 which together act to integrate the red signal reflection pulses. As shown by FIG. 6, the control lead of CMOS switch 258 is connected to point 222, causing the switch to turn on whenever the red LEDs 200 and 201 are energized. The CMOS switch 258 allows the integrator comprised of resistor 260 and red-store capacitor 262 to "see" the output of amplifier 240 only during a narrow 210 microsecond window defined by each pulse at point 222. This prevents integration of unwanted noise along with the desired signal, which would otherwise significantly affect the value stored in red-store capacitor 262.

It will be seen that the control lead of CMOS switch 270, along with the control lead of CMOS switch 258, is connected to point 222. Thus, each voltage pulse across point 222 acts to turn on CMOS switch 270 only during a narrow 210 microsecond window defined by that pulse each time the red LEDs 200 and 201 are energized.

In conjunction with the operation of CMOS switches 258 and 270, the operation of LED emission control amplifier 230 will now be discussed in greater detail. It will be recalled that the output of LED emission control amplifier 230 establishes the collector supply voltage for transistors 218 and 220, and thus dictates the amount of current which flows through LEDs 200, 201, 202 and 203 when they are energized.

Again, with reference to FIG. 6, it will be seen that the non-inverting input of LED emission control amplifier 230 is supplied with a constant reference voltage by virtue of zener diodes 272 and 274, and resistors 276 and 278, which form a voltage divider across zener diode 274. Resistor 280 serves as a dropping or ballast resistor for zener diodes 272 and 274, having one end connected to the cathode of zener diode 272 and its other end connected to the positive supply voltage at point 250. Zener diodes 272 and 274 have a nonimal zener voltage of 1.23 volts. Among the diodes found satisfactory for this purpose are Intersil ICL 8069 Series zener diodes. The resistances of resistors 276 and 278 are chosen to provide a reference voltage of 200 millivolts at the non-inverting input of LED emission control amplifier 230. Varying the ratio of resistors 276 and 278 will vary the depth of penetration of light into the blood.

During the 210 microsecond red-shine cycle window period, CMOS switch 270 is turned on and places the voltage across red-store capacitor 262, representing the amount of light from the red LEDs 200 and 201 reflected back from the blood, at the inverting input of LED emission control amplifier 230. This voltage, in conjunction with the 200 millivolt reference voltage at its non-inverting input, causes its output to assume a voltage sufficient to force the red LEDs 200 and 201 to produce an emission level large enough to result in a predetermined constant level of reflection sensed by phototransistor 204 regardless of the reflectivity of the blood sample being examined. Thus, the opto-electronic feedback loop, comprising LED emission control amplifier 230, transistors 218 and 214, red LEDs 200 and 201, phototransistor 204, amplifier 240, CMOS switch 258, the red-store integrator comprising resistor 260 and red-store capacitor 262, and CMOS switch 270, compensates for varying blood optical density caused by differing hematocrit levels in blood as well as differing oxygen saturation levels.

Without this opto-electrical feedback loop, a constant level of red emission would result in varying reflection levels over the entire blood optical density range. This would produce two deleterious effects. At low hematocrit levels, where blood optical density is low, photons emitted by LED's 200, 201, 202 and 203 would penetrate too far into the blood sample by transmission and would be likely to reflect back from the rear wall of the cuvette and, again by transmission, reach photodetector 204 in addition to the photons properly reflected from the blood. This would obviously cause erroneous readings. On the other end of the spectrum, where blood optical density is relatively high, the reflectivity of the blood will be lower and less light will be reflected to phototransistor 204. As a result of a smaller signal in the presence of the same noise level, the signal to noise ratio would be lower, thus contributing to erroneous readings. In addition, the lack of control of photon penetration depth over these wide ranges of hematocrit levels causes variations in the optical field variables and increases the influence of surface effects, all of which additionally degrade accuracy.

Now the infra-red shine cycle will be discussed, again with reference to FIG. 6. Each time a 210 microsecond voltage pulse appears at point 224, the infra-red LEDs 202 and 203 are energized through resistor 228 and transistors 220 and 216. In the same manner as for the red reflection signal, the infra-red reflection signal, the infra-red reflection signal is presented to and amplified by amplifier 240.

Now, however, CMOS switch 282 rather than CMOS 258, turns on during the 210 microsecond infra-red shine window, and the integrator composed of resistor 284 and infra-red store capacitor 286 integrates the pulses representing the reflected infra-red photons and stores the resultant voltage in infra-red store capacitor 286.

Control of the emission level of the infra-red LEDs 202 and 203 via control of the current flowing through them is accomplished by CMOS switch 288, and LED emission control amplifier 230, in conjunction with voltage reference elements 272, 274, 276, 278 and 280. This time, however, the voltage stored on transfer capacitor 290, rather than that stored on red store capacitor 262, is compared with the 200 millivolt reference voltage by LED emission control amplifier 230. Again, the output voltage of LED emission control amplifier 230 establishes the drive current in the infra-red LED's 202 and 203.

It will be noted that the control lead for CMOS switch 288 is driven by a voltage pulse across resistor 268. This resistor is shared by the emitters of two common collector NPN transistors 264 and 266, whose bases are driven by point 222 and point 224, respectively. The combination of resistor 268 and transistors 264 and 266 will be recognized by those skilled in the art as an OR-gate. Thus, a 210 microsecond pulse will be produced across resistor 268 each time such a pulse appears at either point 222 or point 224.

CMOS switches 270 and 288 together act to charge transfer capacitor 290 during each red-shine cycle. During that cycle, CMOS switches 258, 270 and 288 are turned on. This action connects red-store capacitor 262, which stores a voltage proportional to the red reflection, in series with transfer capacitor 290 and resistors 210 and 212. During the red-shine cycle, resistor 208, in series with the red LEDs 200, has a voltage proportional to the current flowing through the red LEDs 200 and 201 across it. Transfer capacitor 290, which has a capacitance value much less than that of red-store capacitor 262, is charged through resistor 260 to a voltage which is the differential of the voltage stored on red-store capacitor 262 and the voltage pulse across resistor 208. Thus, during the red-shine cycle, transfer capacitor 290 is charged with a voltage representative of the current required by the red LEDs 200 and 201. This voltage is used as a "transfer reference" to set the drive current for the infra-red LEDs, in proportion to that of the red LEDs 200 and 203. It will be appreciated that since, in the ongoing operation of the circuit, none of the capacitors are usually completely discharged, transfer capacitor 290 will have enough time to fully discharge within one 210 microsecond window.

During the infra-red-shine cycle, CMOS switch 288 is again turned on and CMOS switch 270 is turned off. This action places the voltage across transfer capacitor 290 on the inverting input of LED emission control amplifier 230. Since the 200 millivolt reference remains on the non-inverting input of LED emission control amplifier 230, its output assumes a voltage which, via transistors 220 and 216, will cause infra-red LEDs 202 and 203 to emit an amount of light sufficient to maintain the red to infra-red photon output ratio defined by the ratio of resistors 210 and 212 to resistor 208.

It will be appreciated that, during the rest periods in between the 210 microsecond pulses defining red-shine and infra-red-shine cycles, both CMOS switches 270 and 288 are turned off. This condition would normally leave the inverting input of LED emission control amplifier 230 floating during this time period, which could cause the output of that amplifier to either latch up or assume some other unpredictable state. In order to prevent this condition, from which a certain amount of time would be needed for recovery during an active cycle time, the high resistance 291 is provided between the non-inverting input of LED emission control amplifier 230 and the positive end of red-store capacitor 262. In addition, high resistance element 293 is connected between the end of transfer capacitor 290 proximate to the terminal of CMOS switch 288 and the common line 234. The effect of this resistance element is to control any leakage from CMOS switch 288 in the off state which might otherwise affect the voltage stored on transfer capacitor 290.

The red and infra-red-shine cycles which have been disclosed are repetitive. It will be appreciated by those skilled in the art that upon initiating a measurement routine consisting of numerous red and infra-red cycles, the circuit of FIG. 6, due to the one percent duty cycle, passes through a transition period while red-store capacitor 262, infra-red-store capacitor 286, and transfer capacitor 290 charge up to their operating values by pulse integration. Once this charging has occurred, the circuit produces a valid output, which will now be discussed in detail.

During the infra-red-shine cycles, infra-red store capacitor 286 has been charging by pulse integration. Total charging time of the circuit of FIG. 6 is about ten infra-red-shine cycles. Once it has charged to the average value of the voltage pulse produced by amplifier 240 in response to the output of phototransistor 204, infra-red store capacitor 286 has across it a voltage representing the oxygen saturation level of the blood being examined. The higher the saturation level of the blood, the lower will be the voltage across infra-red store capacitor 286.

This result is intuitively obvious to the skilled worker in the art from the operation of this circuit as described herein. As the oxygen content of the blood increases, so does its reflectivity at the red LED wavelength. The opto-electronic feedback circuit described herein acts to decrease the current driving the red LEDs 200 and 201 with increased blood reflectivity in order to maintain a constant level of red reflection photons at phototransistor 204. Since the infra-red LED drive current is tied to the red LED drive currents and thus also decreases, the infra-red LEDs 202 and 203 emit fewer photons under these conditions. Fewer photons are available to be reflected to phototransistor 204, and produce in it a current pulse of lower magnitude and thus a smaller voltage pulse at the input of amplifier 240. This results in a lower voltage pulse at the output of amplifier 240 for integration into infra-red store capacitor 286.

In order to determine the relative saturation level of the blood being examined, it is only necessary to subtract the voltage on infra-red store capacitor 286 from a voltage representing a level of 100% blood oxygen saturation. This operation is performed by amplifer 292. The voltage on infra-red store capacitor 286 appears on the non-inverting input of amplifier 292. A constant voltage exists across zenor diodes 272 and 274, and resistors 294, 296 and 298 and potentiometer 300, which together form a voltage divider. An adjustable reference voltage is made available at the wiper of potentiometer 300 and presented to the non-inverting input of amplifier 292 by a resistor 302. The gain of amplifier 292, set by choosing values for resistors 302 and 304 is chosen to produce an output of zero volts for 0% blood oxygen saturation and minus one volt for 100% blood oxygen saturation at point 306. The output point 306 may be easily connected to a one volt full scale volt meter so that the blood oxygen saturation percentage may be read directly. While a meter of the d'Arsonval movement type will perform adequately, those skilled in the art will recognize the advantages and accuracy obtainable by using a digital volt meter rather than a d'Arsonval movement.

Exemplary parts values for the circuit of FIG. 6 are found in Appendix A, and are intended to be illustrative only. It will be readily understood by those skilled in the art that other component values and types may be used. Capacitors 306 and 308 will be understood as standard power supply filter capacitors. Capacitor 310 is a noise bypass capacitor.

It will be understood by those skilled in the art that locating transistors 218 and 220 on a single substrate, as indicated by dashed line 221, will allow them to compensate for temperature changes in order to maintain accuracy. Other techniques, such as placing the feedback loop components on a thick-film hybrid circuit, are recognized to be conducive to maintaining freedom from inaccuracy caused by thermal drift.

While the above description encompasses a complete blood oxygen saturation meter, users of such devices often want to have available a more versatile instrument. Such an embodiment may be provided by utilizing two circuits, such as those described above, in combination with some additional circuitry, as shown in FIG. 8.

Figure 8:
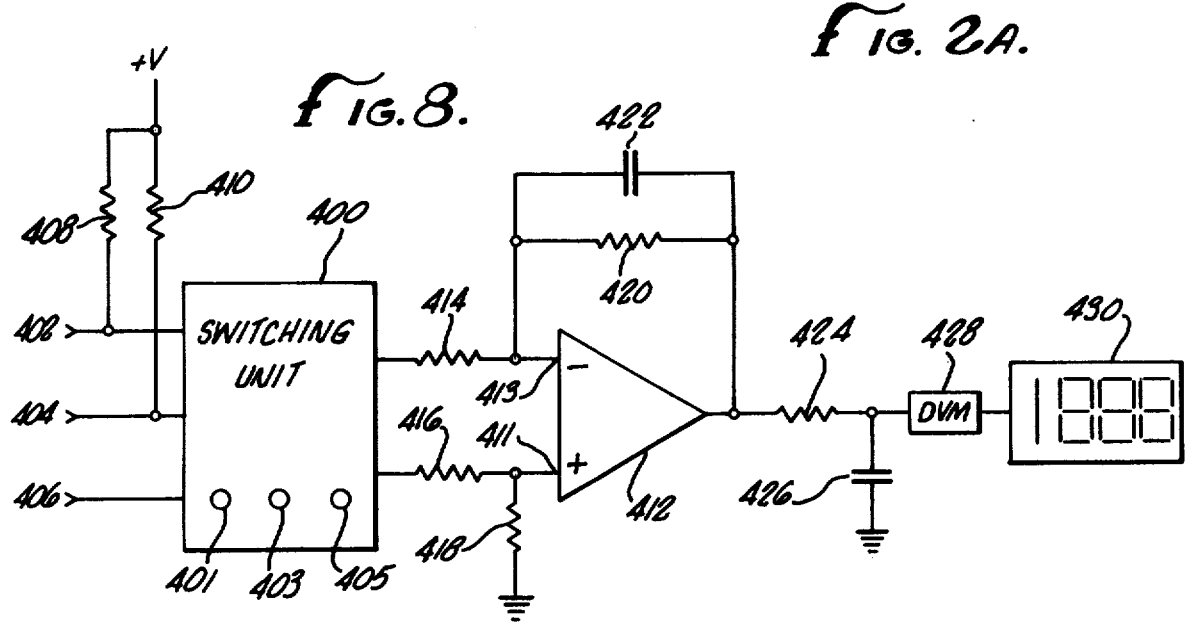
FIG. 8 is a block diagram of a preferred output section of the preferred embodiment of the instant invention showing also an alternate embodiment utilizing fiber optic coupling between the radiation sources, sensor axial blood sample.

The combined embodiment of FIGS. 6 and 8 will, by switch selection, provide direct readings of venous or arterial blood oxygen saturation, or the difference between venous and arterial blood oxygen saturation levels.

Referring now to FIG. 8, a switching unit 400, having input terminals 402 and 404 and a common or ground terminal 406, is shown. Switching unit 400 contains switches for selecting arterial, venous, or differential blood oxygen saturation levels. These switches are numbered 401, 403 and 405 respectively. The outputs 306 of two circuits of the type shown in FIG. 6 are connected, one to input 402 and one to input 404 of switching unit 400. Voltage supply and ground conections are made between all circuits. Pull-up resistors 408 and 410 connect input terminals 402 and 404, respectively, to a source of positive voltage. If a lead wire 306 from a feeder circuit to switching unit 400 is broken or improperly connected, pull-up resistor 408 or 410 will cause an unrealistic reading, to result on the display, thus alerting the equipment operator of the faulty condition.

Switch array 400 provides the inputs of an amplifier 412 with various combinations of its inputs 402 or 404. The operation of switching unit 400 in response to switch selection is as follows. If the switch 403 selecting the venous probe connected to terminal 404 is activated, the non-inverting input 411 of amplifier 412 is connected to the common line 406 and its inverting input 413 is connected to the input terminal 404.

If the switch 401 selecting the arterial probe connected to terminal 402 is activated, the non-inverting input 411 of amplifier 412 is again connected to common line 406, and its inverting input 413 is connected to the input at terminal 402.

If the switch 405 selecting differential mode is activated, the non-inverting input 411 of amplifier 412 is connected to the venous probe input at terminal 404 and the inverting input 413 of amplifier 412 is connected to the arterial probe input at terminal 402. Amplifier 412 is configured to have unity gain by selection of resistors 414, 416, 418, and 420. Capacitor acts as an integrator noise-suppressor to roll off high frequency. If either the venous or arterial mode is selected, this amplifier will invert the signal presented to its input since, for example, an input signal of minus one volt from the circuit of FIG. 6 on either terminal 402 or 404 represents 100% blood oxygen saturation, the output of amplifier 412 will be plus one volt under this condition for that level of blood oxygen saturation. In differential mode, the resultant voltage on the output will usually be positive in polarity since arterial blood oxygen saturation is invariablely higher than venous blood oxygen saturation.

The output of amplifier 412 is fed into an integrator consisting of resistor 424 and capacitor 426. The purpose of this integrator is to present the digital output of display 430 from changing too rapidly. This integrator acts as a damper to improve display continuity and readability. It takes about thirty seconds to reach stability if resistor 424 is selected to be 100k ohms and capacitor 426 is selected to be approximately 23 microfarads by placing two 47 microfarad electrolytic capacitors back to back.

The output of integrator capacitor 426 is connected to the input of a digital volt meter 428, or to a three and one half digit A/D converter (not shown). The output of DVM 428 is connected to a display 430, for direct readout of blood oxygen saturation levels. A conventional one volt full scale d'Arsonval meter movement (not shown) could be substituted for elements 428 and 430, but would, of course, not provide the same measure of accuracy.

It will be appreciated that the preceding examples are merely illustrative of embodiments of this invention, and numerous modifications and variations will suggest themselves to those skilled in the art. More specifically, the invention is not limited to measurement of blood oxygen saturation levels, but may be used to determine other parameters and characteristics of blood which are characterized by predictable changes in the optical density of the blood. Such applications include, but are not limited to, blood contamination, blood compatibility studies, and other conditions such as bacterial infections having the effect of depletion of blood oxygen levels.

Obviously, many other modifications and variations of the present invention are possible in the light of the above teachings. It is therefore to be understood that within the scope of the appended claims, the invention may be practiced otherwise than as specifically described.

I claim:

1. An apparatus for measuring a selected parameter of a blood sample, comprising:
    a first radiation source of a first wavelength;
    a second radiation source of a second wavelength;
    means for positioning said radiation sources to irradiate said sample;
    sensor means responsive to radiation from said sources, having an electrical output and positioned to receive radiation from said sources after reflection from said sample and reject other radiation;
    means for selectively and adjustably energizing said first radiation source such that the amount of its radiation reflected from said sample and received by said sensor means remains substantially constant regardless of the reflectivity of said sample;
    means for selectively and adjustably energizing said second radiation source such that its radiant output is related to the radiant output of said first radiation source;
    circuit means for developing a signal related to the ratio of the reflected radiation received by said sensor means from said first and second radiation sources;
    circuit means responsive to said signal for producing a resultant signal representative of said selected parameter.

2. An apparatus for measuring a selected parameter of a blood sample, comprising:
    a first radiation source of a first wavelength;
    a second radiation source of a second wavelength;
    means for positioning said radiation sources to irradiate said sample;
    sensor means responsive to radiation from said sources, having an electrical output and positioned to receive radiation from said sources after transmission through said sample and reject other radiation;
    means for selectively and adjustably energizing said first radiation source such that the amount of its radiation transmitted through said sample and received by said sensor means remains substantially constant regardless of the transparency of said sample;
    means for selectively and adjustably energizing said second radiation source such that its radiant output is related to the radiant output of said first radiation source;
    circuit means for developing a signal related to the ratio of the transmitted radiation received by said sensor means for said first and second radiation sources;
    circuit means responsive to said signal for producing a resultant signal representative of said selected parameter.

3. The apparatus of claims 1 or 2 wherein the selected parameter is oxygen saturation.

4. The apparatus of claims 1 or 2 further including means for visually displaying said resultant signal.

5. The apparatus of claim 4 wherein said visual display means directly displays the value of said selected parameter.

6. The apparatus of claims 1 or 2 wherein said blood is human blood and said first radiation source has a wavelength in the range of from 8050 Å to 9200 Å and said second radiation source has a wavelength in the range of from 6400 Å to 6800 Å.

7. The apparatus of claim 6 wherein said first radiation source has a wavelength of 9000 Å and said second radiation source has a wavelength of 6600 Å.

8. The apparatus of claim 7 wherein said first and second radiation sources are light emitting diodes.

9. The apparatus of claim 7 wherein said sensor means is a phototransistor.

10. The apparatus of claims 1 or 2 wherein said first and second radiation sources and said sensor means are optically coupled to said sample by fiberoptic means.

11. An apparatus for determining the level of oxygen saturation in extracorporeally circulating blood comprising:
    a cuvette interposed in the flow path of said blood, having a substantially flat, optically clear window area;
    a first radiation source of a first wavelength located proximately to said window;
    a second radiation source of a second wavelength located proximately to said window;
    sensor means located proximately to said window and responsive to radiation from said first and second radiation sources;
    means for selectively and adjustably energizing said first radiation source such that the amount of its radiation reflected from said blood and received by said sensor means remains substantially constant regardless of the reflectivity of said blood;
    means for selectively and adjustably energizing said second radiation source such that its radiant output is related to the radiant output of said first radiation source;
    circuit means for developing a signal related to the ratio of the reflected radiation received by said sensor means from said first and second radiation sources;
    and circuit means responsive to said signal for producing a resultant signal representative of said level of oxygen saturation.

12. The apparatus of claim 11 further including means for visually displaying said resultant signal.

13. The apparatus of claim 12 wherein said visual display means directly displays the oxygen saturation as a percent.

14. The apparatus of claim 13 further including:
    a cuvette in both the venous and arterial flow paths;
    first and second radiation sources and sensor means in proximate location to said windows of both of said cuvettes;
    selection means for selecting measurement of venous or arterial blood oxygen saturation by selectively energizing said first and second radiation sources proximately located to said cuvettes in either the venous or arterial flow paths;

selection means for selecting measurement of venous or arterial blood oxygen saturation;

circuit means for calculating the differential venous and arterial blood oxygen saturation.

15. The apparatus of claims 11, 12, 13 or 14 wherein said blood is human blood and said first radiation source has a wavelength in the range from 8050 Å to 9200 Å and said second radiation source has a wavelength in the range of from 6400 Å to 6800 Å.

16. The apparatus of claim 15 wherein said first radiation source has a wavelength of 9000 Å and said second radiation source has a wavelength of 6600 Å.

17. The apparatus of claim 15 wherein said first and second radiation sources are light emitting diodes.

18. The apparatus of claim 15 wherein said sensor means is a phototransistor.

19. The apparatus of claims 1, 2, or 11 wherein said first and second radiation sources are alternately selected for equal time periods comprising less than 50% duty cycle, each alternate selection being followed by an equal rest period.

20. The apparatus of claim 19 wherein the periods during which said radiation sources are each selected comprise approximately a 1% duty cycle.

21. The apparatus of claim 19 wherein the frequency of selection of each of said radiation sources is a non multiple of 50 or 60 Hz.

22. The apparatus of claims 1, 2, or 11 wherein said means for adjusting said first radiation source is set to control the depth of photon penetration into said blood sample to an average depth of approximately 3 millimeters.

23. The apparatus of claims 1, 2, or 11 wherein said first and second radiation sources are comprised of a plurality of radiation emitters located around said sensor means.

24. The apparatus of claim 23 wherein said plurality of radiation emitters forms a symmetrical pattern about an axis perpendicular to the direction of blood circulation across said window with said sensor means at the center of said axis across said window and wherein said radiation emitters and said sensor means are substantially in contact with said window.

25. The apparatus of claim 24 wherein said plurality of radiation emitters comprises two of said first wavelength and two of said second wavelength.

26. The apparatus of claim 25 wherein said radiation emitters abut one another in a direction transverse to the direction of blood flow and are spaced approximately 5 millimeters from the center of said sensor means in the direction of blood flow, said radiation emitters of the same wavelength being located diagonally from one another.

27. In a blood oxygen saturation meter of the opto-electronic type, including first and second selectively and adjustably energizable light sources of two different wavelengths; sensor means for receiving light emitted by said sensors and transmitted through a blood sample; means for adjusting the output level of this second one of said light sources such that its radiant output is related to the radiant output of the first one of said light sources; and means for determining the ratio of the signals received by said sensor from said light sources; the improvement comprising:

means for selectively and adjustably energizing said first light source such that the amount of its light transmitted through said blood and received by said sensor means remains substantially constant regardless of the transmissibility of said blood.

28. In a blood oxygen saturation meter of the opto-electronic type, including first and second selectively and adjustably energizable light sources of two different wavelengths; sensor means for receiving light emitted by said sources and reflected from a blood sample; means for adjusting the output level of the second one of said light sources such that its radiant output is related to the radiant output of the first one of said light sources; and means for determining the ratio of the signals received by said sensor from said light sources, the improvement comprising:

means for selectively and adjustably energizing said first light source such that the amount of its light reflected from said blood and received by said sensor means remains substantially constant regardless of the transmissibility or reflectivity of said blood.

29. In a blood oxygen saturation meter of the opto-electronic type, including first and second selectively and adjustably energizable light sources of two different wavelengths; sensor means for receiving light emitted by said sensors and transmitted through a blood sample; means for adjusting the output level of this second one of said light sources such that its radiant output is related to the radiant output of the first one of said light sources; and means for determining the ratio of the signals received by said sensor from said light sources; the improvement comprising:

means for selectively and adjustably energizing said first light source such that the amount of its light transmitted through said blood and received by said sensor means remains substantially constant regardless of the transmissibility of said blood; and said first and second light sources are comprised of a plurality of light emitters located around said sensor means.

30. In a blood oxygen saturation meter of the opto-electronic type, including first and second selectively and adjustably energizable light sources of two different wavelengths; sensor means for receiving light emitted by said sources and reflected from a blood sample; means for adjusting the output level of the second one of said light sources such that its radiant output is related to the radiant output of the first one of said light sources; and means for determining the ratio of the signals received by said sensor from said light sources; the improvement comprising:

means for selectively and adjustably energizing said first light source such that the amount of its light reflected from said blood and received by said sensor means remains substantially constant regardless of the reflectivity of said blood; and said first and second light sources are comprised of a plurality of light emitters located around said sensor means.

31. A method for measuring a selected parameter of a blood sample, comprising the steps of:

positioning a first radiation source of a first wavelength and a second radiation source of a second wavelength proximately to said sample;

positioning a sensor means, responsive to radiation from said sources and having an electrical output, proximately to said sample to receive radiation from said sources after reflection from said sample;

selectively and adjustably energizing said first radiation source such that the amount of its radiation reflected from said sample and received by said sensor means remains substantially constant regardless of the reflectivity of said sample;

selectively and adjustably energizing said second radiation source such that its radiant output is related to the radiant output of said first radiation source;

developing a signal related to the ratio of the reflected radiation received by said sensor means from said first and second radiation sources;

producing a resultant signal in response to said signal representative of said selected parameter.

32. A method for measuring a selected parameter of a blood sample, comprising the steps of:

positioning a first radiation source of a first wavelength and a second radiation source of a second wavelength proximately to said sample;

positioning a sensor means, responsive to radiation from said sources and having an electrical output, proximately to said sample to receive radiation from said sources after transmission through said sample;

selectively and adjustably energizing said first radiation source such that the amount of its radiation transmitted through said sample and received by said sensor means remains substantially constant regardless of the transparency of said sample;

selectively and adjustably energizing said second radiation source such that its radiant output is related to the radiant output of said first radiation source;

developing a signal related to the ratio of the transmitted radiation received by said sensor means from said first and second radiation sources;

producing a resultant signal in response to said signal representative of said selected parameter.

33. The method of claims 31 or 32 wherein said selected parameter is oxygen saturation level.

* * * * *